United States Patent [19]

Alig et al.

[11] Patent Number: 4,585,796

[45] Date of Patent: Apr. 29, 1986

[54] NOVEL PHENETHANOLAMINES

[75] Inventors: Leo Alig, Kaiseraugst; Marcel Müller, Frenkendorf, both of Switzerland

[73] Assignee: Hoffmann-La Roche Inc., Nutley, N.J.

[21] Appl. No.: 518,990

[22] Filed: Aug. 1, 1983

[30] Foreign Application Priority Data

Aug. 10, 1982 [CH] Switzerland .................. 4787/82
May 27, 1983 [CH] Switzerland .................. 2897/83

[51] Int. Cl.[4] .............. A61K 31/165; A61K 31/38; C07C 103/28; C07D 333/20
[52] U.S. Cl. .................... 514/620; 562/442; 564/86; 260/465 D; 564/153; 564/156; 514/222; 564/157; 564/165; 514/234; 564/360; 558/413; 514/236; 558/415; 558/422; 514/237; 514/255; 514/330; 514/331; 514/438; 514/522; 514/533; 514/538; 514/563; 514/564; 514/567; 514/603; 514/616; 514/653; 514/654; 514/866; 514/909; 544/59; 544/162; 544/163; 544/386; 544/391; 544/402; 546/226; 546/229; 546/230; 549/75; 560/23
[58] Field of Search .................. 564/165, 360, 86, 153, 564/156, 157; 424/324, 330; 260/465 D; 514/222, 234, 236, 237, 255, 330, 331, 438, 522, 533, 538, 563, 564, 567, 603, 616, 620, 653, 654; 544/59, 162, 163, 386, 391, 402; 546/226, 229, 230; 549/75; 560/23; 562/442

[56] References Cited

U.S. PATENT DOCUMENTS

| | | | |
|---|---|---|---|
| 3,642,896 | 2/1972 | Collin | 260/570.6 |
| 3,644,353 | 2/1972 | Lunts et al. | 260/247.5 R |
| 3,705,233 | 12/1972 | Lunts et al. | 424/45 |
| 3,732,300 | 5/1973 | Lunts et al. | 260/559 S |
| 3,793,365 | 2/1974 | Winter et al. | 564/165 X |
| 3,867,455 | 2/1975 | Atkinson et al. | 260/570.6 |
| 4,101,579 | 7/1978 | Hartley et al. | 564/165 |
| 4,137,328 | 1/1979 | Cox et al. | 564/165 X |

FOREIGN PATENT DOCUMENTS

| | | |
|---|---|---|
| 0006766 | 1/1980 | European Pat. Off. . |
| 0007204 | 1/1980 | European Pat. Off. . |
| 0007205 | 1/1980 | European Pat. Off. . |
| 0007206 | 1/1980 | European Pat. Off. . |
| 0021636 | 1/1981 | European Pat. Off. . |
| 0023385 | 2/1981 | European Pat. Off. . |
| 0025331 | 3/1981 | European Pat. Off. . |
| 0028105 | 5/1981 | European Pat. Off. . |
| 0029320 | 5/1981 | European Pat. Off. . |
| 0040000 | 11/1981 | European Pat. Off. . |
| 0040915 | 12/1981 | European Pat. Off. . |
| 0061907 | 10/1982 | European Pat. Off. . |
| 0063004 | 10/1982 | European Pat. Off. . |
| 0066351 | 12/1982 | European Pat. Off. . |
| 0068669 | 1/1983 | European Pat. Off. . |
| 0070133 | 1/1983 | European Pat. Off. . |
| 0070134 | 1/1983 | European Pat. Off. . |
| 0101069 | 2/1984 | European Pat. Off. ........... 564/360 |
| 2023829 | 9/1971 | Fed. Rep. of Germany ...... 564/165 |
| 2211251 | 7/1974 | France . |
| 45721 | 2/1966 | German Democratic Rep. . |
| 67/5591 | 4/1967 | South Africa . |
| 1109924 | 4/1968 | United Kingdom . |
| 2084577A | 4/1982 | United Kingdom . |

OTHER PUBLICATIONS

Derwent G9045 (South African Patent Specification 66/6722, 1967).
Derwent 54964E (German Democratic Republic Patent Specification 153,682, 1982).
Derwent 79274S (United Kingdom Patent Specification 026523, 1971).
Derwent 27588D (European Patent Specification 26–298, 1981).
Derwent 33331E (European Patent Specification 49–728, 1982).
Derwent 52543V (United Kingdom Patent Specification 1360-457, 1974).
Derwent 46378E (European Patent Specification 52–963, 1982).
Derwent 10299 (Irish Patent Specification 1167/61, 1963).
Derwent 32396 (Nigerian Patent Specification 67,16085, 1968).
Derwent 11381 (French Patent Specification 1353729, 1964).
Derwent 17691 (Belgium Patent Specification 655,285, 1965).
Derwent 9639C (European Patent Specification 7–716, 1980).
Derwent 37625E (European Patent Specification 50–885, 1982).
Derwent 24202 (Netherlands Patent Specification 66,07736, 1966).
Derwent 14848A (Japanese Patent Specification 5 3002-442, 1978).
Derwent 21199 (Belgium Patent Specification 666,985, 1965).
Derwent 4331 (German Patent Specification 1,111,645, 1954).
Derwent 4337 (Belgium Patent Specification 572,661, 1957).
Derwent 4362 (Belgium Patent Specification 612,995, 1961).
Derwent 31,483 (Belgium Patent Specification 703,687, 1968).
Chem. Abst. 81:120718j (1974).
Chem. Abst. 89:146937v (1978).

*Primary Examiner*—Thomas A. Waltz
*Attorney, Agent, or Firm*—Jon S. Saxe; Bernard S. Leon; George W. Johnston

[57] ABSTRACT

The tertiary amines of the formula (Abstract continued on next page.)

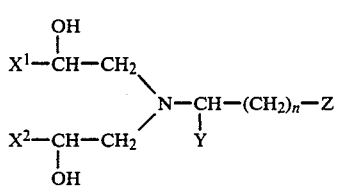

wherein
n represents a whole number of 1 to 5;
X¹ represents phenyl or phenyl mono-, di- or tri-substituted by $R^1$, $R^2$ and $R^3$;
X² represents hydrogen, lower-alkyl, phenyl or phenyl mono-, di- or tri-substituted by $R^1$, $R^2$ and $R^3$;
Y represents hydrogen, lower-alkyl, hydroxymethyl, carboxy or lower-alkoxycarbonyl;
Z represents a group of the formula

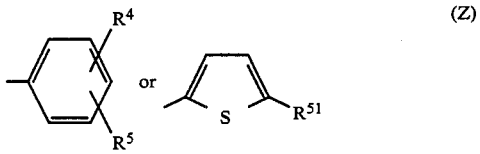

$R^1$, $R^2$ and $R^3$ represent hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonylmethyl;
$R^4$, $R^5$ and $R^{51}$ represent hydrogen, lower-alkyl, lower-alkoxy, lower alkanoyl, carboxy, cyano, hydroxy, hydroxy-lower-alkyl, acyloxy or a group $—C(R^6)=C(R^7)COOR^8$, $—SO_2R^9$, $—C(O)R^9$ or $—CH_2R^{10}$, with the proviso that $R^4$ does not represent hydrogen when $R^5$ represents hydroxy, lower-alkyl or lower-alkoxy;
$R^6$, $R^7$ and $R^8$ represent hydrogen or lower-alkyl;
$R^9$ represents amino, mono-lower-alkylamino or a group R;
R represents di-lower-alkylamino, piperidino, morpholino, thiamorpholino, piperazino or the ether group of a lower aliphatic, cycloaliphatic or araliphatic alcohol or of a phenol; and
$R^{10}$ represents a group R and, where $R^1$, $R^2$ and $R^3$ represent hydrogen, halogen, hydroxy, benzyloxy, lower-alkyl, lower-alkoxy, hydroxymethyl, amino, lower-alkoxybenzylamino or trifluoromethyl and simultaneously Y represents hydrogen, lower-alkyl or hydroxymethyl, $R^{10}$ can also represent amino or mono-lower-alkylamino, have hypoglycaemic activity and reduce glycosuria. They are manufactured from corresponding primary or secondary amines.

31 Claims, No Drawings

NOVEL PHENETHANOLAMINES

BACKGROUND

The present invention is concerned with novel phenethanolamines, a process for their manufacture, novel intermediates therefor and pharmaceutical preparations based on these compounds.

SUMMARY OF THE INVENTION

The phenethanolamines provided by the present invention are compounds of the formula

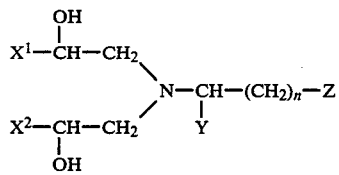

wherein n represents a whole number of 1 to 5;

$X^1$ represents phenyl or phenyl mono-, di- or tri-substituted by $R^1$, $R^2$ and $R^3$;

$X^2$ represents hydrogen, lower-alkyl, phenyl or phenyl mono-, di or tri-substituted by $R^1$, $R^2$ and $R^3$;

Y represents hydrogen, lower-alkyl, hydroxymethyl, carboxy or lower-alkoxycarbonyl;

Z represents a group of the formula

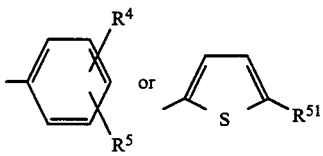

$R^1$, $R^2$ and $R^3$ represent hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonylmethyl;

$R^4$, $R^5$ and $R^{51}$ represent hydrogen, lower-alkyl, lower-alkoxy, lower-alkanoyl, carboxy, cyano, hydroxy, hydroxy-lower-alkyl, acyloxy or a group $-C(R^6)=C(R^7)COOR^8$, $-SO_2R^9$, $-C(O)R^9$ or $-CH_2R^{10}$, with the proviso that $R^4$ does not represent hydrogen when $R^5$ represents hydroxy, lower-alkyl or lower-alkoxy;

$R^6$, $R^7$ and $R^8$ represent hydrogen or lower-alkyl;

$R^9$ represents amino, mono-lower-alkylamino or a group R;

R represents di-lower-alkylamino, piperidino, morpholino, thiamorpholino, piperazino or the ether group of a lower aliphatic, cycloaliphatic or araliphatic alcohol or of a phenol; and $R^{10}$ represents a group R and, where $R^1$, $R^2$ and $R^3$ represent hydrogen, halogen, hydroxy, benzyloxy, lower-alkyl, lower-alkoxy, hydroxymethyl, amino, lower-alkoxybenzylamino or trifluoromethyl and simultaneously Y represents hydrogen, lower-alkyl or hydroxymethyl, $R^{10}$ can also represent amino or mono-lower-alkylamino, and physiologically compatible salts thereof.

The inventive phenethanolamines are useful in the treatment of obesity or diabetes mellitus. In addition, the phenethanolamines can be used for the treatment of conditions associated with an increased protein breakdown such as that occuring during post operative convalescence.

DETAILED DESCRIPTION OF THE INVENTION

The present invention concerns a racemic compound of the formula:

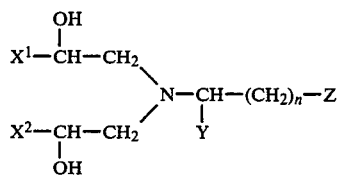

wherein n is an integer of 1 to 5; $X^1$ is a group of the formula:

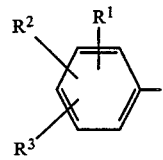

$X^2$ is hydrogen, lower alkyl or a group of the formula:

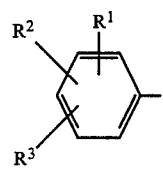

Y is hydrogen, lower-alkyl, hydroxymethyl, carboxy or lower-alkoxycarbonyl; Z is a group of the formula:

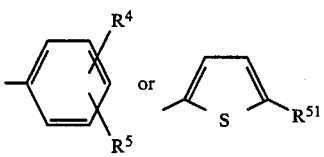

$R^1$, $R^2$ and $R^3$ individually are hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkysulphonylmethyl; $R^4$, $R^5$ and $R^{51}$ individually are hydrogen, lower-alkyl, lower alkoxy, lower-alkanoyl, carboxy, cyano, hydroxy, hydroxy-lower-alkyl, acyloxy, $-C(R^6)=C(R^7)COOR^8$, $-SO_2R^9$, $-C(O)R^9$ or $-CH_2R^{10}$, with the proviso that $R^4$ is not hydrogen when $R^5$ is hydroxy, lower-alkyl or lower-alkoxy; $R^6$, $R^7$ and $R^8$ individually are hydrogen or lower-alkyl; $R^9$ is amino, mono-lower-alkyl-amino or a group R; R is di-lower-alkylamino, piperidino, morpholino, thiamorpholino, piperazino or the ether group of a lower aliphatic, cycloaliphatic or araliphatic alcohol or of phenol; and $R^{10}$ is a group R and when at least one of $R^1$, $R^2$ and $R^3$ is hydrogen, halogen, hydroxy, benzyloxy, lower-alkyl, lower-alkoxy, hydroxymethyl, amino, lower-alkoxybenzylamino or trifluoromethyl and simultaneously Y is hydrogen, lower-alkyl or hydroxymethyl, $R^{10}$ can also be amino or mono-lower-alkylamino; enantiomers or diastereomers thereof; or physiologically compatible salts thereof.

As used herein, alkyl connotes straight or branched chain saturated hydrocarbon groups of 1 to 20 carbon atoms. Lower alkyl denotes alkyl groups of 1 to 6 carbon atoms such as methyl, ethyl, n-propyl, isopropyl n-butyl, isobutyl and hexyl. Lower alkyl groups of 1–4 carbon atoms are preferred. Alkoxy as well as any other groups in the specification containing "alkyl" denote moieties in which their alkyl components are as defined previously. In particular, alkoxy denotes straight or branched chain alkoxy groups of 1 to 20 carbon atoms. Lower alkoxy connotes alkoxy groups having 1 to 6 carbon atoms such as methoxy, ethoxy, isopropoxy, propoxy, butoxy and isobutoxy.

Halogen denotes chlorine, bromine, or iodine, preferably chlorine or bromine.

Aryl denotes mononuclear and polynuclear aromatic hydrocarbon groups which can be unsubstituted or substituted in one or more positions with halogen, nitro, alkylthio, acyloxy, alkoxyalkoxy, lower alkylenedioxy, lower alkyl or lower alkoxy. Suitable mononuclear aromatic hydrocarbon groups are phenyl and the like. Typical polynuclear aromatic hydrocarbon groups are napthyl, anthryl, phenanthryl, azulyl, and the like.

Carboxylic acids are aliphatic, araliphatic and aromatic carboxylic acids of the formula:

wherein A is hydrogen, alkyl, aryl or aralkyl. Preferably A is hydrogen, lower alkyl or phenyl. Examples of carboxylic acids are lower-alkanecarboxylic acids (e.g. formic acid, acetic acid, propionic acid, isopropionic acid, butyric acid), phenyl-lower-alkanecarboxylic acids (e.g. phenylacetic acid) or benzoic acid and the like.

Acyl connotes a radical derived from a carboxylic acid and has the formula:

wherein A is hydrogen, alkyl, aryl or aralkyl. Preferably, A is hydrogen, lower alkyl or phenyl. Typical acyl groups are formyl, acetyl, propionyl, butyryl, benzoyl and the like.

A cycloaliphatic group denotes mononuclear and polynuclear saturated hydrocarbon groups of 1 to 20 carbon atoms. Suitable cycloaliphatic groups include cyclopentyl and cyclohexyl.

An ether group of a lower aliphatic, cycloaliphatic or araliphatic alcohol or of phenol denotes a group of the formula

BO— wherein B is alkyl, cycloalkyl, aralkyl or aryl.
Suitable ether groups include lower alkoxy groups, cycloalkoxy groups (e.g. cyclohexyloxy and cyclopentyloxy), aralkoxy groups (e.g. benzyloxy, substituted benzyloxy such as p-methoxybenzyloxy) and phenoxy and the like.

The compounds of formula I form salts with acids and these salts are also an object of the present invention. Examples of such salts are salts with physiologically compatible mineral acids such as hydrochloric acid, hydrobromic acid, sulphuric acid and phosphoric acid; or with organic acids such as methanesulphonic acid, acetic acid, propionic acid, citric acid, succinic acid, malic acid, fumaric acid, phenylacetic acid or salicylic acid. Carboxylic acids of formula I can also form salts. Examples of such salts are alkali metal, alkaline earth metal, ammonium and alkylammonium salts such as sodium, potassium, calcium, trimethylammonium and ethanolammonium salts.

Unless otherwise indicated the formulae in the specification are shown as racemates. The compounds of formula I contain one or more asymmetric carbon atoms and can accordingly be present as and the invention encompasses optically active enantiomers, diastereomers as well as racemates.

In accordance with the invention, $X^1$ preferably represents phenyl or m-trifluoromethyl-phenyl, especially phenyl. $X^2$ preferably represents phenyl, m-trifluoromethyl-phenyl, lower-alkyl or hydrogen, especially phenyl. Y preferably represents hydrogen or lower-alkyl, especially methyl. $R^4$ preferably represents hydrogen. $R^5$ and $R^{51}$ preferably represent lower-alkanoyl, carbamoyl, sulphamoyl, lower-alkoxycarbonyl or lower-alkylcarbamoyl, especially lower-alkanoyl or carbamoyl. The integer n preferably represents 1 or 2, especially 2.

In accordance with further preferred aspects of the invention, $R^1$ represents hydrogen; $R^2$ and $R^3$ represent hydrogen, halogen, hydroxy, benzyloxy, lower-alkyl, lower-alkoxy, hydroxymethyl, amino, acylamino, lower-alkylbenzylamino, nitro, trifluoromethyl or lower-alkylsulphonylmethyl; $R^4$ represents hydrogen, lower-alkyl, carboxy, cyano, hydroxy, hydroxy-lower-alkyl, acyloxy or a group $—C(R^6)=C(R^7)COOR^8$, $—SO_2R^9$, $—C(O)R^9$ or $—CH_2R^{10}$; and $R^5$ and $R^{51}$ represent carboxy, cyano, hydroxy-lower-alkyl, acyloxy or a group $—C(R^6)=C(R^7)COOR^8$, $—SO_2R^9$, $—C(O)R^9$ or $—CH_2R^{10}$.

The compounds of formula I can be manufactured in accordance with the invention by reacting an epoxide of the formula

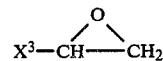

II or a β-keto halide of the formula

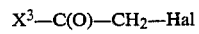

III with an amine of the formula

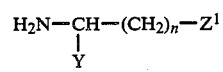

IV or

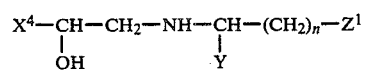

V wherein Hal represents bromine, chlorine or iodine; one of the groups $X^3$ and $X^4$ represents a moiety within group $X^1$ as defined previously and the other represents a moiety within group $X^2$ as defined previously; $Z^1$ represents a group

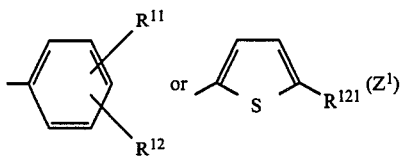

$R^{11}$, $R^{12}$ and $R^{121}$ represents hydrogen, lower-alkyl, lower-alkoxy, lower alkanoyl, carboxy, cyano, hydroxy, hydroxy-lower-alkyl, acyloxy or a group —$C(R^6)$=$C(R^7)COOR^8$, —$SO_2R^9$, —$C(O)R^9$ or —$CH_2R$, with the proviso that $R^{11}$ does not represent hydrogen when $R^{12}$ represents hydroxy, lower-alkyl or lower-alkoxy; and n, $X^1$, $X^2$, Y, R, $R^6$, $R^7$, $R^8$ and $R^9$ have the significance given earlier, $X^3$ representing a group $X^1$ when a compound of formula II or III is reacted with a compound of formula IV; reducing a group $X^1$—C(O)— or $X^2$—C(O)— present in a compound obtained to a group $X^1$—CHOH— or $X^2$—CHOH— and, if desired, functionally modifying a reactive substituent contained in a group $X^1$, $X^2$, Y or $Z^1$ of the reaction product.

The reaction of a compound of formula II with a compound of formula IV or V can be carried out in a known manner for the reaction of epoxides with amines to give aminoalcohols. Conveniently, the reaction partners are brought together in a suitable solvent and heated. As solvents there come into consideration inert organic solvents, for example dimethyl sulphoxide, acetonitrile or ethers such as tetrahydrofuran or dioxan; or alcohols such as ethanol. The reaction temperature is not critical, the reaction conveniently being carried out at temperatures between 60° C. and the boiling point of the reaction mixture.

The reaction of a compound of formula III which a compound of formula IV or V can also be carried out in a known manner, conveniently in the presence of a solvent, preferably an aprotic solvent such as a halogenated hydrocarbon (e.g. chloroform), at a temperature up to 200° C.

Keto groups $X^1$—C(O)— or $X^2$—C(O)— which result in the reaction of a compound of formula III with a compound of formula IV or V are reduced in a known manner to the secondary alcohol groups. This reduction can be carried out under the same conditions as are described hereinafter for the reduction of the compounds of formulae VI-X, the reduction with a complex metal hydride, especially sodium hydride, being preferred because of its selectivity.

A reactive substituent, especially a group —$C(R^6)$=$C(R^7)COOR^8$, —$C(O)R^9$ or —$SO_2R^9$, in the thus-obtained reaction product, viz a compound of formula I in which Z represents a group $Z^1$ as defined earlier, can be functionally modified. The esterification of a carboxyl group can be carried out in a known manner, by means of alkyl halides such as methyl iodide and a base. The saponification of an ester group is conveniently carried out under alkaline conditions, for example by means of aqueous-alcoholic alkali hydroxide (e.g. aqueous-methanolic potassium hydroxide).

A carbamoyl group can be converted into the aminomethyl group by reduction, for example with complex metal hydrides such as lithium aluminium hydride. In an analogous manner, a mono-lower alkylated carbamoyl group can be reduced to the corresponding N-monolower alkylated aminomethyl group.

Starting materials of formula V are known, for example from European Patent Application Nos. 21636 Al and 6735 Al, or can be prepared from known compounds by conventional techniques. The compounds of formula V can be prepared by (a) reacting a compound of the formula

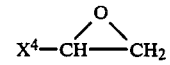  II-1 with a compound of formula IV; or (b) reducing a compound of one of the formulae

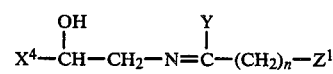 VI

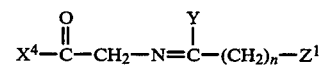 VII

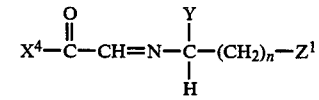 VIII

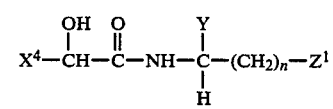 IX

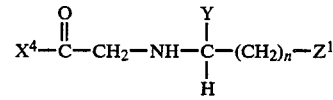 X whereby in the foregoing formulae $X^4$, $Z^1$, Y and n have the significance given earlier.

The reaction of a compound of formula II-1 with a compound of formula IV can be carried out in an inert organic solvent, conveniently a protic solvent such as a lower alkanol (e.g. ethanol). The reaction temperature is not critical; it can lie between room temperature (about 23° C.) and the reflux temperature of the reaction mixture.

The reduction of a compound of formula VI can be carried out by catalytic hydrogenation (e.g. in the presence of noble metal catalysts such as palladium or platinum catalysts) or by treatment with a complex metal hydride such as sodium borohydride. The reaction conditions used can be those which are usual for such reductions. The catalytic hydrogenation is conveniently carried out in an inert organic solvent such as a lower alkanol (e.g. ethanol) at room temperature or at a slightly elevated temperature (e.g. at 20°-80° C.). The reduction with a complex metal hydride is conveniently carried out in a lower alkanol (e.g. methanol) at temperatures of 20°-30° C.

The compounds of formulae VII, VIII, IX and X can be reduced with a complex metal hydride in analogy to the reduction of compounds of formula VI. Sodium borohydride is a suitable complex metal hydride for the reduction of the compounds of formulae VII and VIII. The compounds of formula IX are conveniently reduced with lithium aluminium hydride.

Any racemates within formula I can be separated into their enantiomeric and diastereoisomeric components by conventional techniques. For example, the compounds of formula I having two asymmetric carbon atoms may be separated into diastereoisomeric pairs of enantiomers by, for example, fractional crystallisation from a suitable solvent such as ethyl acetate. The pair of enantiomers thus obtained may be separated into individual stereoisomers by conventional means such as by the use of an optically active acid as a resolving agent.

Alternatively any enantiomer of a compound of formula I may be obtained by stereospecific synthesis using optically pure starting materials of known configuration.

The compounds of formula I and their salts can be used as active substances in pharmaceutical preparations for the treatment of obesity and/or of diabetes mellitus, especially of obese adult diabetics. In an animal experiment an increased catabolism, primarily of fat, has been observed following the administration of compounds of formula I. Furthermore, it has been observed that the compounds of formula I stimulate the formation of brown adipose tissue in rats and obese-hyperglycaemic mice. It is known that defects of the brown adipose tissue play a substantial role in the origin of obesity. In obese-hyperglycaemic mice the compounds of formula I have a pronounced antidiabetic effect, in that they have hypoglycaemic activity and reduce glycosuria. The compounds of formula I exhibit only a slight activity on the working of the heart and circulation.

The dosage for treatment with the inventive compounds depends on the route of administration, age, weight, condition of the patent and the particular condition to be treated. The dosage of compound I can amount to about 0.5–1000 mg, preferably about 2–200 mg, per day for an adult depending on the strength of activity of the individual compounds and on the individual requirements of the patients, whereby the dosage can be administered as a single dosage or in several dosages divided over the day.

In addition, in an animal experiment with the compounds of formula I an increase in the body protein content and a decrease in the fat content could be detected. The compounds of formula I therefore lead to an increase in the lean composition of the body at the expense of fat. Accordingly, the compounds of formula I can be used above all in human medicine for the treatment of conditions which are associated with an increased protein breakdown, for example in convalescence after an operation. In this case the dosages administered are the same as in the treatment of obesity and/or of diabetes mellitus.

The compounds of formula I and their salts can also be used in the maintenance of fattening animals such as beef cattle, pigs, sheep and poultry. In this case the dosages administered and the dosage forms administered can be the same as in the case of vitamins. The compounds of formula I can also be used as feed additives in dosages of about 0.01–100 mg/kg per day depending on the compound, kind of animal and age.

The compounds of formula I and their salts can be used as medicaments in the form of pharmaceutical preparations or compositions.

The pharmaceutical preparations contain at least one of the active substances of formula I or a salt thereof together with a compatible pharmaceutical organic or inorganic carrier material. Any conventional pharmaceutical carrier compatible with phenethanolamines can be utilized. Suitable carriers include, water, gelatine, gum arabic, lactose, starch, magnesium stearate, talc, vegetable oils, polyalkylene glycols, petroleum jelly and the like. The pharmaceutical preparations are preferably administered orally, for example in the form of tablets, capsules, pills, powders, granulates, solutions, syrups, suspensions, elixirs and the like. The administration can, however, also be carried out parenterally, for example in the form of sterile solutions, suspensions or emulsions. The pharmaceutical preparations can be sterilized and/or can contain ingredients such as preserving agents, stabilizers, wetting agents, emulsifiers, salts for varying the osmotic pressure and buffer substances.

In general, compound I amounts to about 2% to about 50% by weight of the inventive pharmaceutical compositions.

The activity of the novel compounds of formula I is evident from the following test results:

(1) Activity on oxygen consumption

Male albino rats weighing 160–180 g were placed in metabolic cages after fasting for 24 hours. The cages were ventilated with a constant 6 liter room air/minute which was equilibrated at a dew point of 11° C. Samples of the spent air were collected during periods of in each case 14 minutes after again equilibrating and the oxygen content and carbon dioxide content were analyzed. After an adaptation time of 4 hours, the animals, divided into groups of 6, received either placebo (5% gum arabic) or the test substance (suspended in 5% gum arabic) per os. Thereafter, the determinations were carried out for a period of 12 hours. In Table I there is given the percentage of the average oxygen consumption after medication as a percentage of control during the first 3 hours and the entire tests duration (12 hours) of the oxygen consumption of the adaptation period, corresponding corrections for variations in the placebo group having been taken into consideration.

Table I tabulate the increased oxygen consumption of the animals administered the inventive compounds over that of the control animals.

TABLE I

| Compound prepared in Example No. | Dosage μM/kg | $O_2$ consumption % of value of the pre-period | |
|---|---|---|---|
| | | 1st–3rd hour | 1st–12th hour |
| 1 | 100 | 156 | 115 |
| 2 | 300 | 143 | 116 |
| 3 | 30 | 127 | 106 |
| 4 | 100 | 175 | 127 |
| 6 | 30 | 140 | 109 |
| 7 | 10 | 125 | 108 |
| 8 | 30 | 184 | 133 |
| 9 | 30 | 124 | 108 |
| 10 | 30 | 130 | 112 |
| 11 | 3 | 116 | 106 |
| 12 | 10 | 190 | 139 |
| 13 | 30 | 146 | 125 |
| 14 | 100 | 182 | 132 |
| 15 | 10 | 125 | 109 |
| 16 | 30 | 127 | 103 |
| 17 | 30 | 172 | 123 |
| 18 | 1 | 146 | 114 |
| 19 | 100 | 148 | 123 |
| 20 | 100 | 149 | 112 |
| 21 | 30 | 130 | 107 |
| 22 | 10 | 113 | 115 |
| 23 | 100 | 121 | 110 |
| 24 | 30 | 154 | 111 |
| 25 | 3 | 155 | 116 |
| 26 | 100 | 43 | 113 |

(2) Catabolic activity on lipids

Groups of 4 male albino rats weighing 320–360 g were kept in metabolic cages without access to feed. Oxygen consumption and carbon dioxide production were measured during 12 hours. After 4 hours, the animals received placebo (5% gum arabic) or the test substance (suspended in gum arabic) per os. In Table II there is given the average decrease of the respiratory quotient ($CO_2/O_2$) during 8 hours after administration of the test substance in comparison to the last 3 hours before administration of the test substance. Variations appearing in the placebo group were taken into consideration in the calculation.

Table II tabulates the decreased respiratory quotient for animals administered the inventive compounds over that of the control animals.

TABLE II

| Compound prepared in Example No. | Dosage μM/kg | Variation of the respiratory quotient |
| --- | --- | --- |
| 11 | 30 | −0.013 |
| 12 | 10 | −0.032 |

(3) Activity on urine glucose and blood glucose and the formation of brown adipose tissue Female hyperglycaemic fat mice were adapted to an amount of feed of 3 g/day/animal. The test compounds (suspended in 5% gum arabic) or placebo (5% gum arabic) were administered orally twice daily during 15 days. Urine was collected for 6 days a week and urine glucose was determined. Blood glucose and the weight of the interscapular brown adipose tissue were determined at the end of the test.

The test results are given in Table III as a percentage of the control value. Table III illustrates the percentage increase in brown adipose tissue formation in animals administered the inventive compound over that in the control animals.

TABLE III

| Compound prepared in Example No. | Dosage μM/kg per day | Urine glucose 1st week/2nd week | | Blood glucose | Brown adipose tissue |
| --- | --- | --- | --- | --- | --- |
| 12 | 60 | 35% | 4% | 50% | 224% |

(4) Activity on protein and fat content of the body

Female hyperglycaemic fatty mice were treated with the test compound for 15 days as described earlier under (3). After completion of the treatment, the composition of the carcass was determined. The results are given in Table IV as a percentage of the carcass weight. Table IV illustrates the increase in protein content and decrease in fat content for animals administered the inventive compound over that in the control animals.

TABLE IV

| Compound prepared in Example No. | Dosage μM/kg/day orally | Protein content | | Fat content | |
| --- | --- | --- | --- | --- | --- |
| | | Control animals | Treated animals | Control animals | Treated animals |
| 12 | 60 | 8.15% | 9.35% | 59.9% | 53.7% |

The following examples illustrate the inventive compounds. Unless otherwise stated, percentages and ratios relating to solvent mixtures are expressed in volume, and the remaining percentages and ratios are expressed in weight. Temperatures are in degrees Celsius (°C.), normal pressure is about 1 atmosphere and room temperature is about 23° C. Unless indicated otherwise, the Examples were carried out as written.

EXAMPLE 1

2.68 g of 5-[3-[[(S)-β-hydroxyphenethyl]amino]propyl]-2-thiophenecarboxamide and 1.5 ml of (R)-phenylethylene oxide were stirred at 95° C. for 24 hours in 37 ml of dimethyl sulphoxide. The mixture was poured into water and extracted three times with methylene chloride. The methylene chloride solutions were washed twice with water, dried and evaporated in vacuo. Chromatography of the residue on silica gel with ether/methanol gave 1.48 g of 5-[3-[[(R)-β-hydroxyphenethyl]-[](S)-β-hydroxyphenethyl]amino]propyl]-2-thiophenecarboxamide; UV: $\epsilon_{277}=10780$.

The 5-[3-[[(S)-β-hydroxyphenethyl]amino]propyl]-2-thiophenecarboxamide used as the starting material was prepared as follows:

2-(p-Toluenesulphonyloxy)propylthiophene (J. Org. Chem. 36, 1971, 2236) was reacted with acetyl chloride and aluminium trichloride in methylene chloride to give 5-acetyl-2-(p-toluenesulphonyloxy)propylthiophene.

Therefrom there was obtained with sodium azide in dimethyl sulphoxide 5-(3-azidopropyl)-2-thienyl methyl ketone. Oxidation with hypobromide gave 5-(3-azidopropyl)-2-thiophenecarboxylic acid of melting point 71°–72°. Reaction of this acid with thionyl chloride and subsequent treatment with concentrated ammonia gave 5-(3-azidopropyl)-2-thiophenecarboxamide of melting point 85°–87°. Therefrom there is obtained, after treatment with triphenylphosphine and hydrolysis (J. Org. Chem. 40, 1975, 1659), 5-(3-aminopropyl)-2-thiophenecarboxamide of melting point 143.5°–144° (from water).

5-(3-Aminopropyl)-2-thiophenecarboxamide was heated with (S)-phenylethylene oxide at b 95° in dimethyl sulphoxide. The mixture was diluted with water and methylene chloride and the aqueous phase was extracted twice with methylene chloride. The methylene chloride phases were washed with water, dried over sodium sulphate and evaporated in vacuo. Chromatography of the residue with methanol on silica gel gave 5-[3-[[(S)-β-hydroxyphenethyl]amino]propyl]-2-thiophenecarboxamide of melting point 94°–96°; $[\alpha]_{589}=+19°$ (c=0.1% in dioxan); $\epsilon_{256}=8490$; $\epsilon_{275}=10780$.

EXAMPLE 2

5 g of 5-(3-aminopropyl)-2-thiophenecarboxamide and 3.4 ml of (S)-phenylethylene oxide were stirred at 95° for 26 hours in 68 ml of dimethyl sulphoxide. The mixture was poured into 200 ml of water and extracted three times with 150 ml of methylene chloride. The methylene chloride solutions were washed with water, dried and evaporated in vacuo. Chromatography of the residue on silica gel with ether/methanol gave 2.85 g of 5-[3-[bis-[(S)-β-hydroxyphenethyl]amino]propyl]-2-thiophenecarboxamide; $[\alpha]_D=+76°$ (c=0.1% in dioxan); UV: $\epsilon_{277}=10390$.

EXAMPLE 3

750 mg of 5-(3-aminopropyl)-2-thiophenecarboxamide and 0.47 ml of (±)-phenylethylene oxide were heated to boiling for 4 hours in 4.7 ml of ethanol. After evaporation of the solvent in vacuo, the residue was chromatographed on silica gel with ether/methanol. There were obtained 400 mg of 5-[3-[bis-(β-hydroxyphenethyl)amino]propyl]-2-thiophenecarboxamide; UV: $\epsilon_{277}=11250$.

EXAMPLE 4

30 g of 5-(3-aminopropyl)-2-thiophenecarboxamide and 20.2 ml of (R)-phenylethylene oxide were stirred at 95° for 24 hours in 400 ml of dimethyl sulphoxide. After cooling, the mixture was diluted with 1.3 l of water and extracted three times with about 600 ml of methylene chloride. The methylene chloride solutions were washed twice with water, dried over sodium sulphate and evaporated in vacuo. Chromatography of the residue on silica gel with ether/methanol gave 21 g of 5-[3-[bis[(R)-β-hydroxyphenethyl]amino]propyl]-2-thiophenecarboxamide; UV: $\epsilon_{276}=9900$; $[\alpha]_D=-69°$ (c=0.1% in dioxan).

EXAMPLE 5

In accordance with Example 3, from methyl 4-(3-aminopropyl)benzoate and (±)-phenylethylene oxide there was obtained methyl p-[3-[bis](β-hydroxyphenethyl)amino]propyl]benzoate as an amorphous substance; $\epsilon_{238}=17520$.

EXAMPLE 6

In accordance with Example 3, from 4-(3-aminopropyl)benzamide and (±)-phenylethylene oxide there was obtained p-[3-[bis-(β-hydroxyphenethyl)amino]propyl]benzamide; amorphous; $\epsilon_{236}=14270$.

EXAMPLE 7

In accordance with Example 3, from 4-(3-aminopropyl)benzamide and (R)-phenylethylene oxide there was obtained p-[3-bis-[[(R)-β-hydroxyphenethyl]amino]propyl]benzamide; $\epsilon_{234}=14240$.

EXAMPLE 8

In accordance with Example 3, from (S)-1-methyl-3-(4-aminocarbonylphenyl)propylamine and (R)-styrene oxide there was obtained p-[(S)-3-[bis-[(R)-β-hydroxyphenethyl]amino]butyl]benzamide as an amorphous substance; $\epsilon_{235}=14130$; $[\alpha]_D^{20}=-28°$ (c=0.5% in methanol).

EXAMPLE 9

In accordance with Example 3, from 4-(3-aminopropyl)benzenesulphonamide and (R)-styrene oxide there was obtained p-[3-[bis-[(R)-β-hydroxyphenethyl]amino]propyl]benzenesulphonamide as an amorphous substance; $\epsilon_{225}=16820$; $[\alpha]_D^{20}=-60°$ (c=1.0% in methanol).

The 4-(3-aminopropyl)benzenesulphonamide used as the starting material was prepared as follows:

p-Aminosulphonylbenzaldehyde was reacted with diethyl cyanomethyl-phosphonate/sodium hydride in tetrahydrofuran to give 1-cyano-2-(4-aminosulphonylphenyl)-ethane which was hydrogenated in methanol with Raney-cobalt as the catalyst to give 4-(3-aminopropyl)benzenesulphonamide.

EXAMPLE 10

In accordance with Example 3, from (R)-1-methyl-3-(4-aminocarbonylphenyl)propylamine and (S)-phenylethylene oxide there was obtained p-[(R)-3-[bis-[(S)-β-hydroxyphenethyl]amino]butyl]benzamide as a colourless amorphous substance; $\epsilon_{235}=14230$; $[\alpha]_D^{20}=+45°$ (c=1.0% in methanol).

EXAMPLE 11

In accordance with Example 3, from (R)-1-methyl-3-(4-aminosulphonylphenyl)propylamine and R-styrene oxide there was obtained p-[(R)-3-[bis-[(R)-β-hydroxyphenethyl]amino]butyl]benzenesulphonamide as an amorphous substance; $\epsilon_{224}=17410$; $[\alpha]_D^{20}=-95°$ (c=0.5% in methanol).

EXAMPLE 12

In accordance with Example 3, from (R)-styrene oxide and (R)-1-methyl-3-(4-aminocarbonylphenyl)-propylamine there was obtained p-[(R)-3-[bis-[(R)-β-hydroxyphenethyl]amino]butyl]benzamide; $\epsilon_{234}=14490$; $[\alpha]_D^{20}=-99°$ (c=0.8% in methanol).

EXAMPLE 13

In accordance with Example 3, from (R)-styrene oxide and (S)-1-methyl-3-(4-aminosulphonylphenyl)-propylamine there was obtained p-[(S)-3-[bis-[(R)-β-hydroxyphenethyl]amino]butyl]benzenesulphonamide as an amorphous substance; $\epsilon_{232}=14820$; $[\alpha]_D^{20}=-13°$ (c=0.5% in methanol).

The (S)-1-methyl-3-(4-aminosulphonylphenyl)-propylamine used as the starting material was prepared as follows:

4-(4-Aminosulphonylphenyl)butanone-2 was reacted with (S)-(−)-α-phenylethylamine and p-toluenesulphonic acid as the catalyst in toluene with separation of water to give the Schiff's base (S)-N-(α-methylbenzyl)-1-methyl-3-(4-aminosulphonylphenyl)propylimine. The imine was hydrogenated in methanol in the presence of Raney-nickel to give a mixture of the optical isomers of N-(α-methylbenzyl)-1-methyl-3-(4-aminosulphonylphenyl)propylamine. The amine was converted with oxalic acid into a mixture of the oxalates from which there was obtained by two-fold crystallization pure (S)-1-methyl-3-(4-aminosulphonylphenyl)propylamine oxalate of melting point 123°-127°; $[\alpha]_D^{20}=-68°$ (c=1.0% in methanol). Hydrogenolysis of this substance in alcohol under 4 bar of hydrogen at 60° for 24 hours yielded pure (S)-1-methyl-3-(4-aminosulphonylphenyl)propylamine.

EXAMPLE 14

5 ml of ethylene oxide were added while stirring to a suspension, cooled to 0°, of 1.0 g of p-[3-[[(R)-β-hydroxyphenethyl]amino]propyl]benzamide in 20 ml of 90% ethanol. All had dissolved after stirring at +5° for 30 minutes, whereupon the solution was held at +5° for a further 20 hours. For the working-up, the solvent and excess ethylene oxide were removed by evaporation in vacuo and the residue was chromatographed over 100 g of silica gel. With ethyl acetate/methanol (95:5) there was eluted 1.0 g of pure amorphous p-[3-[(2-hydroxyethyl)-[(R)-β-hydroxyphenethyl]amino]propyl]benzamide; $[\alpha]_D^{20}=-44°$ (c=0.5% in methanol); $\epsilon_{236}=13700$.

EXAMPLE 15

In accordance with Example 3, from (S)-1-methyl-3-(4-methylaminocarbonylphenyl)propylamine and (R)-styrene oxide there was obtained p-[(S)-3-[bis-[(R)-α-hydroxyphenethyl]amino]butyl]-N-methylbenzamide as an amorphous substance; $[\alpha]_D^{20}=-22°$ (c=1.0% in methanol); $\epsilon_{235}=12800$.

EXAMPLE 16

In accordance with Example 14, from p-[3-[[(R)-β-hydroxyphenethyl]amino]propyl]benzamide and propylene oxide (1,2-epoxypropane) there was obtained p-[3-[[(R)-β-hydroxyphenethyl]-[(R,S)-2-hydroxypropyl]amino]propyl]benzamide as an amorphous substance; $[\alpha]_D^{20} = -40°$ (c=0.4% in methanol).

EXAMPLE 17

In accordance with Example 14, from p-[(S)-3-[[(R)-β-hydroxyphenethyl]amino]-butyl]benzamide and ethylene oxide there was obtained p-[(S)-3-[(2-hydroxyethyl]-[(R)-β-hydroxyphenethyl]amino]butyl]benzamide as an oil; $[\alpha]_D^{20} = -18°$ (c=0.5% in methanol).

EXAMPLE 18

In accordance with Example 14, from p-[(R)-3-[[(R)-β-hydroxyphenethyl]amino]butyl]benzamide and ethylene oxide there was obtained p-[(R)-3-[(2-hydroxyethyl)-[(R)-β-hydroxyphenethyl]amino]butyl]benzamide as a colourless oil; $[\alpha]_D^{20} = -76°$ (c=0.3% in methanol).

EXAMPLE 19

850 mg of 5-[3-[bis-[(R)-β-hydroxyphenethyl]amino]propyl]-2-thiophenecarboxamide and 300 mg of lithium aluminum hydride were boiled at reflux for 1.5 hours in 60 ml of tetrahydrofuran. The mixture was treated cautiously with 2N sodium hydroxide solution and extracted three times with ether. The ether solutions were washed neutral with water, dried and evaporated. Chromatography of the residue on silica gel with methanol gave 650 mg of 5-[3-[bis-[(R)-β-hydroxyphenethyl]amino]propyl]-2-aminomethyl-thiophene.

EXAMPLE 20

In accordance with Example 14, from p-[3-[[(R)-β-hydroxyphenethyl]amino]propyl]benzenesulphonamide and ethylene oxide there was obtained p-[3-[(2-hydroxyethyl)-[(R)-β-hydroxyphenethyl]amino]propyl]benzenesulphonamide as a colourless oil; $[\alpha]_D^{20} = -39°$ (c=0.3% in methanol); $\epsilon_{224} = 14720$.

The p-[3-[[(R)-β-hydroxyphenethyl]amino]propyl]benzenesulphonamide used as the starting material was prepared as follows:

A mixture of 20 g of 4-(3-aminopropyl)benzenesulphonamide, 16.8 g of (R)-styrene oxide and 500 ml of acetonitrile was heated under reflux for 40 hours. The solvent was then removed by evaporation in vacuo and the residue was chromatographed on 1 kg of silica gel. With chloroform/n-propanol25% ammonia (1600:100:4) there could be isolated 8.3 g of pure p-[3-[[(R)-β-hydroxyphenethyl]amino]propyl]benzenesulphonamide of melting point 165°–166° (from acetonitrile); $[\alpha]_D^{20} = -13.4°$ (c=1.0% in methanol); $\epsilon_{224} = 14710$.

EXAMPLE 21

In accordance with Example 3, from 4-(3-aminopropyl)benzonitrile and (R)-styrene oxide there was obtained p-[3-[bis-[(R)-β-hydroxyphenethyl]amino]propyl]benzonitrile as a colourless oil; $[\alpha]_D^{20} = -57°$ (c=0.4% in methanol); $\epsilon_{232} = 17570$.

EXAMPLE 22

In accordance with Example 3, from methyl p-[(R)-2-aminopropyl]-β-methyl-cinnamate and 3-trifluoromethyl-styrene oxide there was obtained methyl p-[(R)-2-bis-[(RS)-β-hydroxy-m-(trifluoromethyl)phenethyl]-propyl]-β-methyl-cinnamate; $[\alpha]_D^{20} = -53°$ (c=0.2% in methanol); $\epsilon_{276} = 18500$.

EXAMPLE 23

In accordance with Example 3, from p-[(S)-2-aminopropyl]benzoic acid and (R)-styrene oxide there was obtained p-[(S)-2,2-bis-[[(R)-β-hydroxyphenethyl]amino]propyl]benzoic acid; $[\alpha]_D^{20} = -3°$ (c=0.5% in methanol); $\epsilon_{233} = 11700$.

EXAMPLE 24

In accordance with Example 3, from p-[(S)-2-aminopropyl]benzamide and styrene oxide there was obtained p-[(S)-2,2-bis-[[(R)-β-hydroxyphenethyl]amino]propyl]benzamide; $[\alpha]_D^{20} = -1°$ (c=0.8% in methanol); $\epsilon_{226} = 11700$.

EXAMPLE 25

In analogy to Example 4, from (RS)-5-(3-aminobutyl)-2-thiophenecarboxide and (R)-phenylethylene oxide there was obtained 5-[(RS)-3-[bis-[(R)-β-hydroxyphenethyl]amino]butyl]-2-thiophenecarboxamide; $[\alpha]_D = -90°$ (c=0.1% in dioxan); UV: $\epsilon_{277} = 11100$; $\epsilon_{255} = 8700$.

The (RS)-5-(3-aminobutyl)-2-thiophenecarboxamide as the starting material was prepared as follows:

4-(5-Acetyl-2-thienyl)-2-butanone (Tetrahedron 35, 1979, 329) was reacted with ethylene glycol, triethyl orthoformate and p-toluenesulphonic acid in methylene chloride to give methyl 5-[2-(2-methyl-1,3-dioxolan-2-yl)ethyl]-2-thienyl ketone. Oxidation with sodium hypobromite and subsequent hydrolysis gave 5-(3-oxobutyl)-2-thiophenecarboxylic acid. With sodium borohydride there was obtained therefrom 5-(3-hydroxybutyl)-2-thiophenecarboxylic acid which was converted in dimethylacetamide with methyl iodide and sodium carbonate into the methyl ester. Treatment with p-toluenesulphochloride in pyridine and reaction with sodium azide in dimethyl sulphoxide gave methyl 5-(3-azidobutyl)-2-thiophenecarboxylate from which there was obtained by saponification the corresponding acid. The acid was treated with thionyl chloride to give the acid chloride from which there was obtained with concentrated ammonia in ether 5-(3-azidobutyl)-2-thiophenecarboxamide. Reduction of the azido group with triphenylphosphine and subsequent hydrolysis gave (RS)-5-(3-aminobutyl)-2-thiophenecarboxamide of melting point 65°–75°; $\epsilon_{256} = 7780$; $\epsilon_{275} = 9900$.

EXAMPLE 26

Likewise as in Example 25, from p-(2-aminoethyl)benzamide and (R)-phenylethylene oxide there was obtained p-[2-[bis-[(R)-β-hydroxyphenethyl]amino]ethyl]benzamide; $[\alpha]_D = -59°$ (c=0.1% in dioxan); UV: $\epsilon_{234} = 13500$.

The p-(2-aminoethyl)benzamide used as the starting material was prepared as follows:

p-(2-Bromoethyl)-acetophenone (J.A.C.S. 62, 1940, 1435) was reacted with sodium azide in dimethyl sulphoxide to give p-(2-azidoethyl)acetophenone. Oxidation with sodium hypobromide gave p-(2-azidoethyl)benzoic acid (melting point 130°–131°, from acetone/hexane) which was converted with thionyl chloride into the corresponding acid chloride. Treatment of the acid chloride with ammonia gave p-(2-azidoethyl)benzamide. Treatment with triphenylphosphine and hydrolysis gave p-(2-aminoethyl)benzamide of melting point 132°–133° (from ethanol).

EXAMPLE 27

In analogy to Example 4, from (R)-phenylethylene oxide and 5-(2-aminoethyl)-2-thiophenecarboxamide there was obtained 5-[2-[bis-[(R)-β-hydroxyphenethyl-]amino]ethyl]-2-thiophenecarboxamide; $[\alpha]_D^{20} = -61°$ (c=0.1% in dioxan); $\epsilon_{277} = 10560$.

The 5-(2-aminoethyl)-2-thiophenecarboxamide used as the starting material was prepared as follows:

2-(2-Thienyl)ethyl p-toluenesulphonate (J.A.C.S. 95, 1973, 1247), acetyl chloride and aluminum chloride were reacted in methylene chloride to give 2-[(5-acetyl-2-thienyl)ethyl] p-toluenesulphonate (melting point 111°–112°, from ethanol). This was converted with sodium azide in dimethyl sulphoxide into 5-(2-azidoethyl)-2-thienyl methyl ketone. Oxidation with sodium hypobromite yielded 5-(2-azidoethyl)-2-thiophenecarboxylic acid of melting point 53°–55°. Treatment of this acid with thionyl chloride gave the corresponding acid chloride which was reacted with ammonia to give 5-(2-azidoethyl)-2-thiophenecarboxyamide (melting point 104°–105°, from ethanol). Reaction of this amide with triphenylphosphine and hydrolysis (J. Org. Chem. 40, 1975, 1659) gave 5-(2-aminoethyl)-2-thiophenecarboxamide of melting point 134°–136° (from acetonitrile).

EXAMPLE 28

In analogoy to Example 4, from (R)-phenylethylene oxide and 5-[(RS)-2-aminopropyl]-2-thiophenecarboxamide there was obtained 5-[(RS)-2-[bis-[(R)-β-hydroxyphenethyl]amino]propyl]-2-thiophenecarboxamide; $[\alpha]_D^{20} = -58°$ (c=0.1% in dioxan); $\epsilon_{279} = 8450$.

The 5-[(RS)-2-aminopropyl]-2-thiopheneccarboxamide used as the starting material was prepared as follows:

α-Methyl-2-thiophenethanol (J.A.C.S. 64, 1942, 477), acetyl chloride and aluminum chloride were reacted in methylene chloride to give (RS)-2-(5-acetyl-2-thienyl)-1-methylethyl acetate. This was saponified with sodium hydroxide in methanol to give 5-[(RS)-2-hydroxypropyl]-2-thienyl methyl ketone which was subsequently reacted with p-toluenesulphochloride to give (RS)-2-(5-acetyl-2-thienyl)-1-methylethyl p-toluenesulphonate of melting point 101°–103°. Therefrom there was obtained with sodium azide in dimethyl sulphoxide 5-[(RS)-2-azidopropyl]-2-thienyl methyl ketone which was oxidized in bromine in sodium hydroxide to give 5-[(RS)-2-azidopropyl]-2-thiophenecarboxylic acid. This acid was converted with thionyl chloride into the corresponding acid chloride from which there was obtained by treatment with ammonia 5-[(RS)-2-azidopropyl]-2-thiophenecarboxamide of melting point 79°–80° (from ether). Treatment of this amide with triphenylphosphine and hydrolysis gave 5-[(RS)-2-aminopropyl]-2-thiophenecarboxamide of melting point 91°–92° (from acetonitrile).

EXAMPLE 29

In analogy to Example 4, from (RS)-5-(3-aminobutyl)-2-thiophenecarboxamide and m-(trifluoromethyl)phenylethylene oxide there was obtained 5-[(RS)-3-[bis-[(RS)-β-hydroxy-m-(trifluoromethyl)phenethyl]amino]butyl]-2-thiophenecarboxamide; $\epsilon_{272} = 11840$.

EXAMPLE 30

5 g of ethyl (E)-5-[(RS)-2-aminopropyl]-β-methyl-2-thiopheneacrylate and 3.7 g of m-(trifluoromethyl)phenylethylene oxide were stirred at 90° for 22 hours in 50 ml of dimethyl sulphoxide. A further 1.23 g of m-(trifluoromethyl)phenylethylene oxide were added and the mixture was heated to 90° for a further 19 hours. The working-up was carried out in analogy to Example 4. Chromatography on silica gel gave ethyl (E)-5-[(RS)-2-[bis-[(RS)-β-hydroxy-m-(trifluoromethyl)phenethyl]amino]propyl]-β-methyl-2-thiopheneacrylate; $\epsilon_{323} = 17310$.

The ethyl (E)-5-[(RS)-2-aminopropyl]-β-methyl-2-thiopheneacrylate used as the starting material was prepared as follows:

5-[(RS)-2-hydroxyprpyl]-2-thienyl methyl ketone and triethyl phosphonoacetate were reacted in alcohol in the presence of sodium ethylate to give ethyl (E)-5-[(RS)-2-hydroxypropyl]-β-methyl-2-thiopheneacrylate. With p-toluenesulphochloride there was obtained therefrom ethyl (E)-β-methyl-5-[(RS)-2-[(p-toluenesulphonyl)oxy]propyl]-2-thiopheneacrylate (melting point 121°, from methylene chloride/alcohol). Reaction of this ester with sodium azide in dimethyl sulphoxide gave ethyl (E)-5-[(RS)-2-azidopropyl]-β-methyl-2-thiopheneacrylate. Reduction of the latter ester with triphenylphosphine and hydrolysis led to ethyl (E)-5-[(RS)-2-aminopropyl]-β-methyl-2-thiopheneacrylate; $\epsilon_{320} = 17970$.

EXAMPLE 31

In analogy to Example 30, from ethyl (E)-5-[(RS)-3-aminobutyl]-β-methyl-2-thiopheneacrylate and (R)-phenylethylene oxide there were obtained
ethyl (E)-5-[(R)-3-[bis-[(R)-β-hydroxyphenethyl]amino]butyl]-β-methyl-2-thiopheneacrylate; $[\alpha]_D^{20} = -126°$ (c=0.1% in dioxan); $\epsilon_{324} = 19030$; and
ethyl (E)-5-[(S)-3-[bis-[(R)-β-hydroxyphenethyl]amino]butyl]-β-methyl-2-thiopheneacrylate; $[\alpha]_D^{20} = -40°$ (c=0.1% in dioxan); $\epsilon_{323} = 18050$.

The ethyl (E)-5-[(RS)-3-aminobutyl]-β-methyl-2-thiopheneacrylate used as the starting material was prepared as follows:

(RS)-4-(2-thienyl)-2-butanol (Coll. Czech. Chem. Comm. 41, 1976, 479), acetyl chloride and aluminum chloride were reacted in methylene chloride to give (RS)-3-(5-acetyl-2-thienyl)-1-methylpropyl acetate. This was saponified with sodium hydroxide in methanol to give (RS)-5-(3-hydroxybutyl)-2-thienyl methyl ketone. This was reacted in alcohol with triethyl phosphonoacetate in the presence of sodium alcoholate to give ethyl (E)-5-[(RS)-3-hydroxybutyl]-β-methyl-2-thiopheneacrylate. Reaction with p-toluenesulphochloride and subsequent treatment with sodium azide gave ethyl (E)-5-[(RS)-3-azidobutyl]-β-methyl-2-thiopheneacrylate. Therefrom there was obtained by reduction with triphenylphosphine and subsequent hydrolysis ethyl (E)-5-[(RS)-3-aminobutyl]-β-methyl-2-thiopheneacrylate; $\epsilon_{320} = 17465$.

EXAMPLE 32

In analogy to Example 4, from m-(trifluoromethyl)phenylethylene oxide and p-(2-aminoethyl)-benzamide there was obtained p-[2-[bis-[(RS)-β-hydroxy-m-(trifluoromethyl)phenethyl]amino]ethyl]benzamide; $\epsilon_{232} = 14200$.

EXAMPLE 33

In analogy to Example 4, from (R)-phenylethylene oxide and 2-acetyl-5-[(RS)-2-aminopropyl]thiophene there was obtained 5-[(RS)-2-[bis-[(R)-β-hydroxyphenethyl]amino]propyl]-2-thienyl methyl ketone; $[\alpha]_D^{20} = -46°$ (c=0.1% in methanol); $\epsilon_{298} = 10400$; $\epsilon_{263} = 7250$.

The 2-acetyl-5-[(RS)-2-aminopropyl]thiophene used as the starting material can be prepared by reacting 5-[(RS)-2-azidopropyl]-2-thienyl methyl ketone with triphenylphosphine and subsequently hydrolyzing the product with aqueous ammonia.

EXAMPLE 34

In analogy to Example 30, from ethyl (E)-5-[(RS)-2-aminopropyl]-β-methyl-2-thiopheneacrylate and (R)-phenylethylene oxide there were obtained ethyl (E)-5-[(R)-2-[bis-[(R)-β-hydroxyphenethyl]amino]propyl]-β-methyl-2-thiopheneacrylate; $[\alpha]_D^{20} = -76°$ (c=0.1% in methanol); $\epsilon_{324} = 18690$; and ethyl (E)-5-[(S)-2-[bis-[(R)-β-hydroxyphenethyl]amino]propyl]-β-methyl-2-thiopheneacrylate; $[\alpha]_D^{20} = +18°$ (c=0.1% in methanol), $\epsilon_{325} = 18250$.

EXAMPLE 35

In analogy to Example 30, from methyl 5-[(RS)-3-aminobutyl]-2-thiophenecarboxylate and (R)-phenylethylene oxide there were obtained methyl 5-[(R)-3-[bis-[(R)-β-hydroxyphenethyl]amino]butyl]-2-thiophenecarboxylate; $[\alpha]_D^{20} = -103°$ (c=0.1% in methanol); $\epsilon_{279} = 13180$; $\epsilon_{255} = 9540$; and methyl 5-[(S)-3-[bis-[(R)-β-hydroxyphenethyl]amino]butyl]-2-thiophenecarboxylate; $[\alpha]_D^{20} = -18°$ (c=0.1% in methanol); $\epsilon_{279} = 12150$; $\epsilon_{255} = 8914$.

The methyl 5-[(RS)-3-aminobutyl]-2-thiophenecarboxylate used as the starting material can be prepared by reacting methyl 5-(3-azidobutyl)-2-thiophenecarboxylate with triphenylphosphine in pyridine and hydrolyzing the reaction product with concentrated ammonia to give methyl 5-[(RS)-3-aminobutyl]-2-thiophenecarboxylate; $\epsilon_{278} = 11280$; $\epsilon_{254} = 8760$.

EXAMPLE 36

In accordance with Example 2, from methyl p-(3-aminopropyl)benzoate and (R)-styrene oxide there was obtained methyl p-[bis-[(R)-hydroxyphenethyl]amino]propyl]benzoate as an amorphous substance; $[\alpha]_D^{20} = -60°$ (c=1.0% in methanol); $\epsilon_{238} = 13770$.

EXAMPLE 37

In accordance with Example 2, from p-[(R)-2-aminopropyl]benzamide and (R)-styrene oxide there was obtained p-[(R)-2-[bis-[(R)-β-hydroxyphenethyl]amino]propyl]benzamide in amorphous form; $[\alpha]_D^{20} = -102°$ (c=0.71% in methanol); $\epsilon_{232} = 13780$.

EXAMPLE 38

In accordance with Example 2, from (R)-1-methyl-3-(4-aminocarbonylphenyl)propylamine and m-trifluoromethyl-styrene oxide there was obtained p-[(R)-3-[bis-[(RS)-β-hydroxy-m-(trifluoromethyl)phenethyl]amino]butyl]benzamide as an amorphous substance; $[\alpha]_D^{20} = -20°$ (c=1.0% in methanol); $\epsilon_{235} = 14990$.

EXAMPLE 39

In accordance with Example 2, from methyl p-[(R)-2-aminopropyl]-benzoate and styrene oxide there was obtained methyl p-[2-[bis-[(R)-hydroxyphenethyl]amino]propyl]benzoate (amorphous); $[\alpha]_D^{20} = -91$ (c=0.6% in methanol); $\epsilon_{237} = 15720$.

EXAMPLE 40

A mixture of 13.6 g of 4-amino-3,5-dichlorophenacyl bromide and 4.6 g of (R)-1-methyl-3-(4-aminocarbonylphenyl)propylamine in 100 ml of chloroform was warmed to 50° for 3 hours. The mixture was evaporated in vacuo, the residue was dissolved in 200 ml of methanol was 70 ml of water and a solution of 3.0 g of sodium borohydride in 20 ml of water was added dropwise thereto while cooling with ice and stirring so that the temperature did not rise above 20°. After completion of the addition, the mixture was stirred at 5°-10° for a further 2 hours, then poured into ice-water and extracted with methylene chloride. The material isolated from the methylene chloride extract was chromatographed on silica gel. With chloroform/n-propanol/25% ammonia (1000:10:1) there was obtained pure p-[(R)-3-[bis-[(RS)-4-amino-3,5-dichloro-β-hydroxyphenethyl]amino]butyl]benzamide in amorphous form; $[\alpha]_D^{20} = -46°$ (c=1.0% in methanol); $\epsilon_{242} = 31080$; $\epsilon_{302} = 7250$.

EXAMPLE 41

In accordance with Example 2, from (R)-styrene oxide and 2-(3,4-dimethoxyphenyl)ethylamine there was obtained α,α'-[[(3,4-dimethoxyphenyl)imino]dimethylene]bis-[(R)benzylalcohol] in amorphous form; $[\alpha]_D^{20} = -52°$ (c=1,0% in Methanol); $\epsilon_{230} = 11020$, $\epsilon_{280} = 3090$.

EXAMPLE 42

In accordance with Example 2, from 4-benzyloxystyrene oxide and 2-(3,4-dimethoxyphenyl)ethylamine there was obtained α,α'-[[3,4-dimethoxyphenyl)imino]-dimethylene]bis[(RS)-p-benzyloxy-benzylalcohol] in amorphous form; $\epsilon_{226} = 37930$, $\epsilon_{274} = 6970$, $\epsilon_{280} = 6610$.

EXAMPLE 43

Tablets having the following composition can be manufactured in the usual manner:

| | |
|---|---|
| Active substance of formula I, e.g. p-[(R)—3-[bis-[(R)—β-hydroxyphenethyl]-amino]butyl]benzamide | 250 mg |
| Lactose | 200 mg |
| Maize starch | 300 mg |
| Maize starch paste | 50 mg |
| Calcium stearate | 5 mg |
| Dicalcium phosphate | 45 mg |

EXAMPLE 44

A solution of 216 mg of p-[(R)-3-[bis-[(R)-β-hydroxyphenethyl]amino]butyl]benzamide in 2 ml of methanol was reacted with 58 mg of fumaric acid. After addition of 10 ml of ether to the solution, there were obtained 210 mg of p-[(R)-3-[bis[(R)-β-hydroxyphenethyl]amino]butyl]benzamide fumarate, which after crystallization from acetonitril, has a melting point of 92°-94°; $[\alpha]_D^{20} = -81°$ (c=1,0 in methanol); $\epsilon_{234} = 17400$.

EXAMPLE 45

In a manner similar to that of Example 44, there was obtained p-[(R)-3-[bis-[(R)-β-hydroxyphenethyl]amino]butyl]benzamide maleate of melting point 127°–128° (in methanolether); $[\alpha]_D^{20} = -78°$ (c=0,8 in methanol); $\epsilon_{232} = 16900$.

We claim:

1. A racemic compound of the formula:

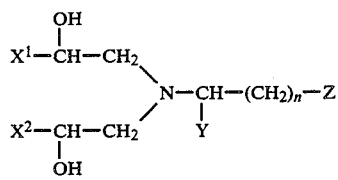

wherein n is an integer of 1 to 5; $X^1$ is a group of the formula:

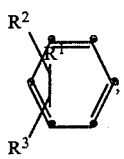

$X^2$ is hydrogen, lower alkyl or a group of the formula:

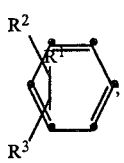

Y is hydrogen, lower-alkyl, hydroxymethyl, carboxy or lower-alkoxycarbonyl; Z is a group of the formula:

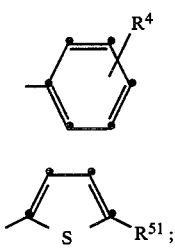

$R^1$, $R^2$ and $R^3$ individually are hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonyl-methyl; $R^4$ and $R^{51}$ individually are lower-alkanoyl, carboxy, cyano, hydroxy-lower-alkyl, acyloxy, —C($R^6$)=C($R^7$)—COOR$^8$, —SO$_2$R$^9$, —C(O)R$^9$ or —CH$_2$R$^{10}$; $R^6$, $R^7$ and $R^8$ individually are hydrogen or lower alkyl; $R^9$ is amino, mono-lower-alkylamino or a group R; R is di-loweralkylamino, piperidino, morpholino, thiamorpholino, piperazino, or the ether group of a lower aliphatic, cycloaliphatic or araliphatic alcohol or of phenol; and $R^{10}$ is the group R and, when at least one of $R^1$, $R^2$ and $R^3$ is hydrogen, halogen, hydroxy, benzyloxy, lower-alkyl, lower-alkoxy, hydroxymethyl, amino, lower-alkoxybenzylamino or trifluoromethyl and simultaneously Y is hydrogen, lower-alkyl or hydroxymethyl, $R^{10}$ can also be amino or mono-lower-alkylamino, enantiomers or diastereomers thereof, or physiologically compatible salts thereof.

2. The compound of claim 1, wherein the compound is p-[(S)-3-[(2-hydroxyethyl)-[(R)-β-hydroxyphenethyl-]amino]butyl]benzamide.

3. The compound of claim 1 wherein $R^1$ is hydrogen.

4. The compound of claim 3 wherein $R^2$ and $R^3$ individually are hydrogen, halogen, hydroxy, benzyloxy, lower-alkyl, lower-alkoxy, hydroxymethyl, amino, acylamino, lower-alkylbenzylamino, nitro, trifluoromethyl or lower-alkylsulphonylmethyl.

5. The compound of claim 4, wherein $R^4$ and $R^{51}$ individually are carboxy, cyano, hydroxy-lower-alkyl, acyloxy, —C($R^6$)=C($R^7$)COOR$^8$, —SO$_2$R$^9$, —C(O)R$^9$ or —CH$_2$R$^{10}$.

6. The compound of claim 1 wherein n is 1 or 2.

7. The compound of claim 6 wherein n is 2.

8. The compound of claim 1 wherein $X^1$ is phenyl or m-trifluoromethyl-phenyl.

9. The compound of claim 8 wherein $X^1$ is phenyl.

10. The compound of claim 1 wherein $X^2$ is phenyl, m-trifluoromethyl-phenyl, lower-alkyl or hydrogen.

11. The compound of claim 10 wherein $X^2$ is phenyl.

12. The compound of claim 1 wherein Y is hydrogen or lower-alkyl.

13. The compound of claim 12 wherein Y is hydrogen.

14. The compound of claim 12 wherein Y is lower alkyl.

15. The compound of claim 14 wherein Y is methyl.

16. The compound of claim 15 wherein $R^4$ and $R^{51}$ individually are lower-alkanoyl, carbamoyl, sulphamoyl, lower-alkoxycarbonyl or lower-alkylcarbamoyl.

17. The compound of claim 16 wherein $R^4$ and $R^{51}$ individually are lower-alkanoyl or cabamoyl.

18. The compound of claim 1 wherein n is 1 or 2; $X^1$ is phenyl or m-trifluoromethyl-phenyl; $X^2$ is phenyl, m-trifluoromethyl-phenyl, lower-alkyl or hydrogen; Y is hydrogen or lower-alkyl; $R^4$ and $R^{51}$ individually are lower-alkanoyl, carbamoyl, sulphamoyl, lower-alkoxycarbonyl or lower-alkylcarbamoyl.

19. The compound of claim 18 wherein n is 2; $X^1$ and $X^2$ are phenyl; Y is methyl; $R^4$ and $R^{51}$ individually are lower-alkanol or carbamoyl.

20. The compound of claim 19 wherein Z is

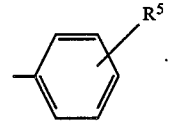

21. The compound of claim 19, p-[(R)-3-[bis-[(R)-β-hydroxyphenethyl]-amino]butyl]-benzamide.

22. The compound of claim 19 wherein Z is

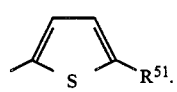

23. A method for treating obesity in a mammal comprising administering to said mammal a racemic compound of the formula:

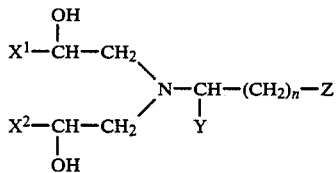

wherein n is an integer of 1 to 5; $X^1$ is a group of the formula:

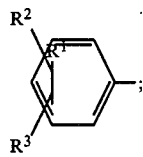

$X^2$ is hydrogen, lower alkyl or a group of the formula:

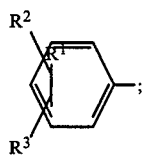

Y is hydrogen, lower-alkyl, hydroxymethyl, carboxy or loweralkoxycarbonyl; Z is a group of the formula:

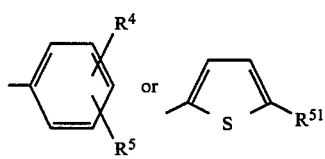

$R^1$, $R^2$ and $R^3$ individually are hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonylmethyl; $R^4$, $R^5$ and $R^{51}$ individually are hydrogen, lower-alkyl, lower alkoxy, lower-alkanoyl, carboxy, cyano, hydroxy, hydroxy-lower-alkyl, acyloxy, $-C(R^6)=C(R^7)COOR^8$, $-SO_2R^9$, $-C(O)R^9$ or $-CH_2R^{10}$, with the proviso that $R^4$ is not hydrogen when $R^5$ is hydroxy, lower-alkyl or lower-alkoxy; $R^6$, $R^7$ and $R^8$ individually are hydrogen or lower-alkyl; $R^9$ is amino, mono-lower-alkylamino or a group R; R is di-lower-alkylamino, piperidino, morpholino, thiamorpholino, piperazino, or the ether group of a lower aliphatic, cycloaliphatic or araliphatic alcohol or of phenol; and $R^{10}$ is a group R and, when at least one of $R^1$, $R^2$ and $R^3$ is hydrogen, halogen, hydroxy, benzyloxy, lower-alkyl, lower-alkoxy, hydroxymethyl, amino, lower-alkoxybenzylamino or trifluoromethyl and simultaneously Y is hydrogen, lower-alkyl or hydroxymethyl, $R^{10}$ can also be amino or mono-lower-alkylamino,
an enantiomer or diastereomer thereof, or a physiologically compatible salt thereof, in an amount which is effective as an anti-obesity agent.

24. The method of claim 23, wherein the compound is p-[(R)-3-[bis[(R)-β-hydroxyphenethyl]amino]butyl]-benzamide.

25. The method of claim 23, wherein the compound is p-[(S)-3-[(2-hydroxyethyl)-[(R)-β-hydroxyphenethyl]amino]butyl]benzamide.

26. A method for treating diabetes mellitus in a mammal comprising administering to said mammal a racemic compound of the formula:

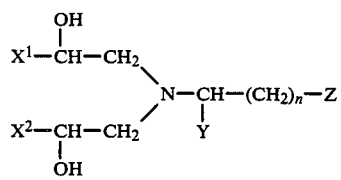

wherein n is an integer of 1 to 5; $X^1$ is a group of the formula:

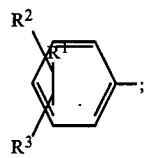

$X^2$ is hydrogen, lower alkyl or a group of the formula:

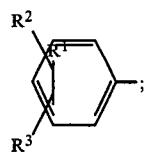

Y is hydrogen, lower-alkyl, hydroxymethyl, carboxy or lower-alkoxycarbonyl; Z is a group of the formula:

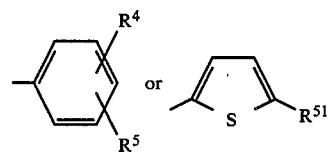

$R^1$, $R^2$ and $R^3$ individually are hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonylmethyl; $R^4$, $R^5$ and $R^{51}$ individually are hydrogen, lower-alkyl, lower alkoxy, lower-alkanoyl, carboxy, cyano, hydroxy, hydroxy-lower-alkyl, acyloxy, $-C(R^6)=C(R^7)COOR^8$, $-SO_2R^9$, $-C(O)R^9$ or $-CH_2R^{10}$, with the proviso that $R^4$ is not hydrogen when $R^5$ is hydroxy, lower-alkyl or lower-alkoxy; $R^6$, $R^7$ and $R^8$ individually are hydrogen or lower-alkyl; $R^9$ is amino, mono-lower-alkylamino or a group R; R is di-lower-alkylamino, piperidino, morpholino, thiamorpholino, piperazino, or the ether group of a lower aliphatic, cycloaliphatic or araliphatic alcohol or of phenol; and $R^{10}$ is a group R and, when at least one of $R^1$, $R^2$ and $R^3$ is hydrogen, halogen, hydroxy, benzyloxy, lower-alkyl, lower-alkoxy, hydroxymethyl, amino, lower-alkoxybenzylamino or trifluoromethyl and simultaneously Y is hydrogen, lower-alkyl or hydroxymethyl, $R^{10}$ can also be amino or mono-lower-alkylamino, an enantiomer or diastereomer thereof, or a physiologically compatible salt thereof, in an amount which is effective as an anti-diabetes mellitus agent.

27. The method of claim 26, wherein the compound is p-[(R)-3-[bis[(R)-β-hydroxyphenethyl]amino]butyl]-benzamide.

28. The method of claim 26, wherein the compound is p-[(S)-3-[(2-hydroxyethyl)-[(R)-β-hydroxyphenethyl]amino]butyl]benzamide.

29. A method for increasing the body protein content in a mammal, particularly in a fattening animal, comprising administering to said mammal a racemic compound of the formula

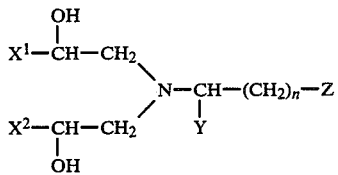

wherein n is an integer of 1 to 5; $X^1$ is a group of the formula:

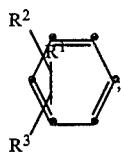

$X^2$ is hydrogen, lower alkyl or a group of the formula:

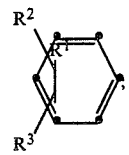

Y is hydrogen, lower-alkyl, hydroxymethyl, carboxy or lower-alkoxycarbonyl; Z is a group of the formula:

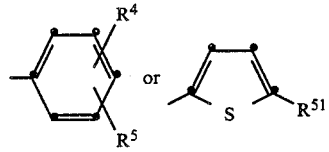

$R^1$, $R^2$ and $R^3$ individually are hydrogen, halogen, hydroxy, benzyloxy, lower-alkyl, lower-alkoxy, hydroxymethyl, amino, acylamino, lower-alkoxybenzylamino, nitro, carbamoyl, trifluoromethyl or lower-alkylsulphonyl-methyl; $R^4$, $R^5$ and $R^{51}$ individually are hydrogen, lower-alkyl, lower alkoxy, lower-alkanoyl, carboxy, cyano, hydroxy, hydroxy-lower-alkyl, acyloxy, —C($R^6$)=C($R^7$)COOR$^8$, —SO$_2$R$^9$, —C(O)R$^9$ or —CH$_2$R$^{10}$, with the proviso that $R^4$ is not hydrogen when $R^5$ is hydroxy, lower-alkyl or lower-alkoxy; $R^6$, $R^7$, and $R^8$ individually are hydrogen or lower-alkyl; $R^9$ is amino, mono-lower-alkylamino or a group R; R is di-lower-alkylamino, piperidino, morpholino, thiamorpholino, piperazino, or the ether group of a lower aliphatic, cycloaliphatic or araliphatic alcohol or of phenol; and $R^{10}$ is a group R and, when at least one of $R^1$, $R^2$ and $R^3$ is hydrogen, halogen, hydroxy, benzyloxy, lower-alkyl, lower-alkoxy, hydroxymethyl, amino, lower-alkoxybenzylamino or trifluoromethyl and simultaneously Y is hydrogen, lower-alkyl or hydroxymethyl, $R^{10}$ can also be amino or mono-lower-alkylamino, an enantiomer or diastereomer thereof, or a physiologically compatible salt thereof, in an effective body protein increasing amount.

30. The method of claim 29, wherein the compound is p-[(R)-3-[bis[(R)-β-hydroxyphenethyl]amino]butyl]-benzamide.

31. The method of claim 29, wherein the compound is p-[(S)-3-[(2-hydroxyethyl)-[(R)-β-hydroxyphenethyl]amino]butyl]benzamide.

* * * * *

UNITED STATES PATENT AND TRADEMARK OFFICE
CERTIFICATE OF CORRECTION

PATENT NO. : 4,585,796
DATED : April 29, 1986
INVENTOR(S) : Leo Alig and Marcel Muller It is certified that error appears in the above—identified patent and that said Letters Patent is hereby corrected as shown below:

Column 19, lines 16-23; lines 28-32;

Column 21, lines 14-18;

Column 21, lines 23-29;

Column 22, lines 19-25; lines 30-35;

Column 23, lines 40-45; and

Column 24, lines 1-8;

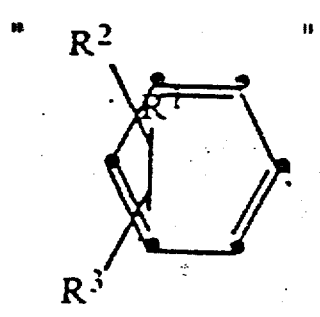 should be 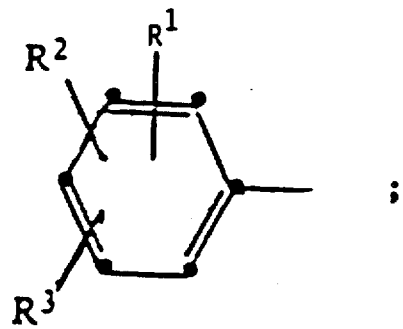 ;

Signed and Sealed this

Eighteenth Day of December, 1990

*Attest:*

HARRY F. MANBECK, JR.

*Attesting Officer*     *Commissioner of Patents and Trademarks*